United States Patent [19]

Musolf et al.

[11] 4,096,742

[45] Jun. 27, 1978

[54] FLEXING DEVICE FOR TESTING RESILIENT ARTICLES AND METHOD OF COMPRESSION TESTING

[75] Inventors: Thomas Carl Musolf; Harold Thomas Wyman, both of Southgate, Mich.

[73] Assignee: BASF Wyandotte Corporation, Wyandotte, Mich.

[21] Appl. No.: 769,355

[22] Filed: Feb. 16, 1977

[51] Int. Cl.$^2$ ............................................. G01N 3/10
[52] U.S. Cl. ................................................... 73/94
[58] Field of Search .................... 73/94, 90, 91, 92, 81

[56] References Cited

U.S. PATENT DOCUMENTS

| | | | |
|---|---|---|---|
| 2,376,814 | 5/1945 | Robinson | 73/94 |
| 3,095,733 | 7/1963 | Sjostrom | 73/91 |
| 3,508,159 | 4/1970 | Marpe | 73/91 |
| 3,786,676 | 1/1974 | Korolyshun et al. | 73/94 |
| 3,793,880 | 2/1974 | Sugi et al. | 73/91 |

*Primary Examiner*—Anthony V. Ciarlante

*Attorney, Agent, or Firm*—Robert J. Henry; Bernhard R. Swick; Robert E. Dunn

[57] ABSTRACT

A method of compression testing resilient articles comprising the steps of cutting a sample to desired predetermined dimensions, placing the sample in a preflexing machine to provide preflexing at test specifications, and testing the preflexed sample in a sophisticated compression testing machine. The preflexing machine uses a fluid operated cylinder to move a pressure foot member into and out of the sample to compress same the desired number of times, at the desired rate of deflection and desired number of compressions at a fixed total proportion of compression. The machine is automated through a stepping switch driven in steps by a pulse operated drive mechanism which receives pulses from limit switches associated with the movement of the pressure foot. The stepping switch controls the cylinder through solenoids operating a switching valve means to alternately supply fluid pressure on each side of the piston in the cylinder. Parameters may be varied by control of the fluid pressure and the size and position of the sample.

8 Claims, 7 Drawing Figures

FLEXING DEVICE FOR TESTING RESILIENT ARTICLES AND METHOD OF COMPRESSION TESTING

BACKGROUND OF THE INVENTION

1. Field of the Invention

The present invention relates to a flexing device for testing resilient articles and to a method of compression testing. More particularly, the invention relates to a method of utilizing compression testing machinery more efficiently, and to a new machine component utilized in the method of the invention.

2. Description of the Prior Art

It is well known to provide tests on foamed articles such as foamed rubber and foamed urethane in order to test for the desired strength characteristics. One of the test utilized is a compression load test and various machines have been developed for making this test.

For example, U.S. Pat. No. 2,245,060 shows a compression testing machine that utilizes a pressure foot carried on a hydraulic cylinder. The machine contains an elaborate mechanism for assuring accurate measurements of compressive forces. U.S. Pat. No. 3,786,676 shows another machine used for measuring load deflection on foam rubber. This machine uses servomotors, which drive to a null balance, to provide the desired compression. The compressive force is read automatically on a calibrated voltmeter.

In conducting such tests on urethane foam, it is part of the test procedure to compress the foam twice before taking the compression test. Prior to this invention, the sample was placed in a test machine similar in operation to those in the cited patents, and the test machine utilized to provide the preliminary compressions or preflexing, and then the test measurement was made. The machine utilized for the final test contains considerable mechanism to drive the pressure foot through servomotors, and also contains the associated measuring devices for measuring the final compressive forces. In addition, the procedure required an operator to manually operate the machine through the preflexing operation.

SUMMARY OF THE INVENTION

It is a primary object of the present invention to save both operator time and wear and use time of an expensive machine by providing an improved procedure for compression testing.

Thus in accordance with the invention, a test method is provided in which the test sample is cut to accurately predetermined dimensions, the sample is then placed in a preflexing device formed to provide the desired compressive depth in a controlled speed rate for the desired number of compressions, and then the preflexed sample is measured in a standard compression tester.

In this way, the use of the expensive compression tester is saved for use in testing only. In addition, operator time is saved by using an automated machine for the preflexing step. By making use of a separate machine for preflexing, a simpler machine can be built which is also automated to carry out the entire preflexing program.

Therefore, it is another object of the invention to provide a machine for use in compression testing to automatically carry out the preflexing test procedure.

Although test procedures generally do become standardized, the requirements may vary with changes in procedures or materials. Therefore, it is important to provide a machine that may easily accommodate such changes. In accordance with the invention, a machine is provided that can accommodate samples of different thickness or provide different extents of compression. In addition, the compressive rate may also be adjusted. In the event that the number of compressions should change, the programming control is separate and can be easily replaced or modified.

Thus, it is a further object of the invention to provide a preflexing machine that can be easily adjusted or modified to carry out any of various preflexing specifications automatically.

Therefore, in accordance with the invention there is provided a flexing device for use in testing flexible foam articles comprising a bed for receiving samples in a testing position,
support means carried on the bed,
a fluid operated cylinder mounted on said support means,
said cylinder comprising a piston, a first passage means for providing fluid to one side of the piston, a second passage means for providing fluid to the other side of the piston, and a pressure foot member attached to the piston and mounted to move into the testing position,
conduit means for carrying fluid to and from said first and second passage means,
a source of fluid under pressure in communication with said conduit means,
an exhaust means,
switching valve means for supplying fluid under pressure to one of said first and second passage means and for switching fluid from the other of said first and second passage means to said exhaust means,
circuit means for operating the switching valve means comprising a stepping switch, solenoid means for operating the switching valve in positions corresponding to positions of the stepping switch, and a pulse operated drive mechanism for driving the stepping switch,
first switch means mounted on said support means for actuation on an extended movement of the piston, and
a second switch means mounted on said support means for actuation on a retracted movement of the piston
said first and second switch means being located to provide pulses to said pulse operated drive mechanism whereby the stepping switch is moved at each end of the movement of the piston for providing automatic operation through the stepping switch sequence.

DESCRIPTION OF THE DRAWINGS

In the accompanying drawings, in which like parts are identified by the same numerals throughout.

Figure 1:
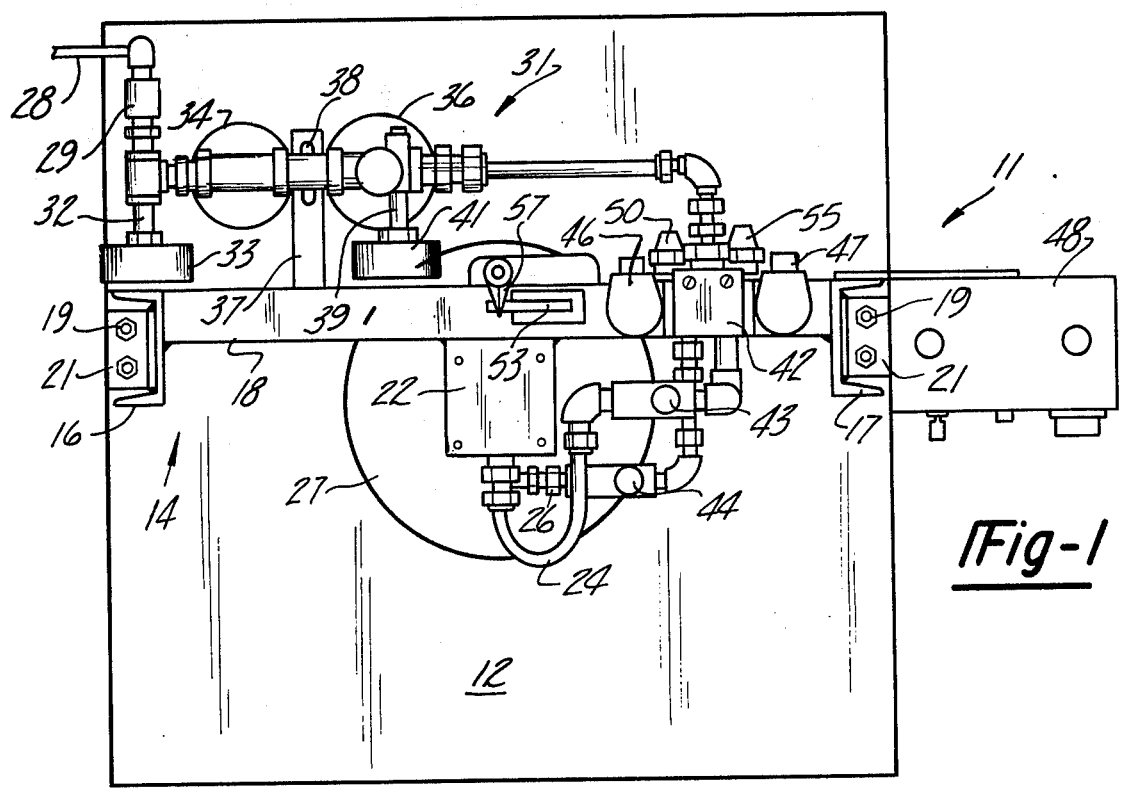
FIG. 1 is a plan view of a preflexing machine made in accordance with the invention.

While only the preferred embodiment is shown in the drawings, it should be understood that various changes may be made without departing from the spirit and scope of the appended claims.

DESCRIPTION OF THE PREFERRED EMBODIMENT

Figure 2:
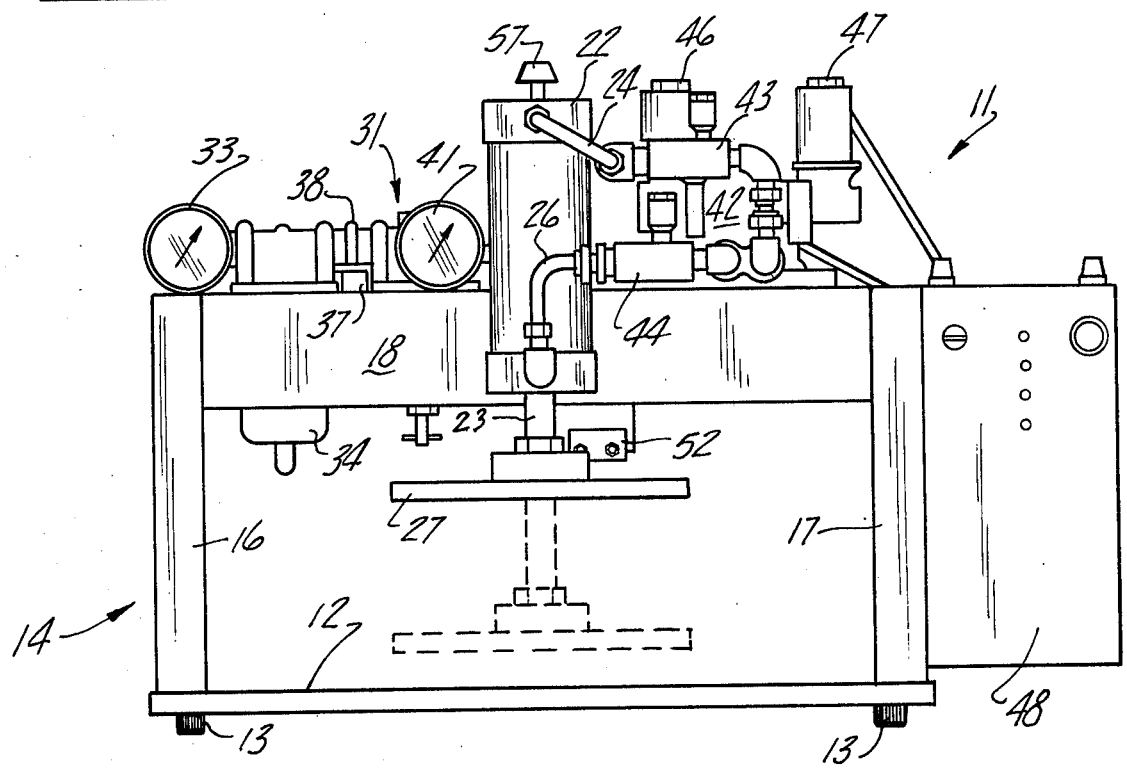
FIG. 2, a front view of the machine of FIG. 1.
Figure 3:
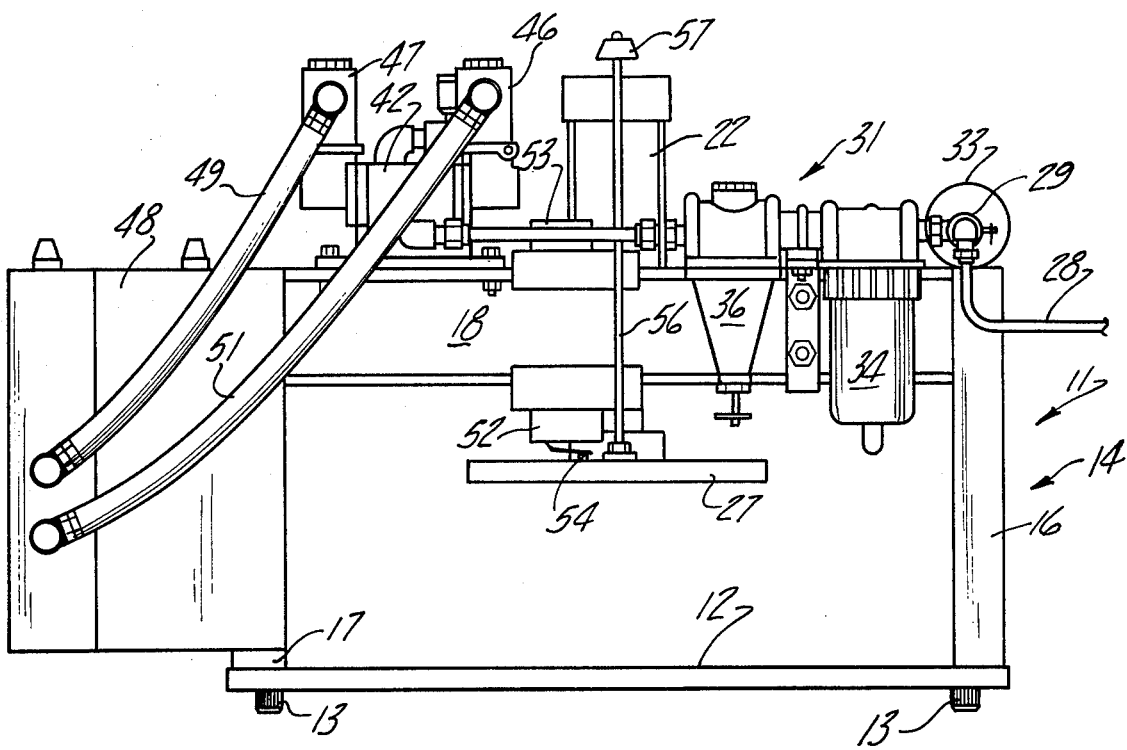
FIG. 3, a rear view of the machine of FIG. 1.

Referring more particularly to the drawings, there is shown in FIGS. 1 through 3, a preflexing machine 11 formed with a flat table 12 carried on suitable legs 13. Appropriately fixed to the table, a support means in the form of frame 14 is provided. As here shown, frame 14 consists of two upright channel members 16 and 17 and a horizontal channel beam 18, all welded together, with the frame bolted to the table through fasteners 19 and brackets 21, the brackets 21 being welded to the channel members 16 and 17.

An air cylinder 22 is securely attached to the horizontal channel member 18, to provide a strong secure fixed relation to table 12. The air cylinder is conventional in structure and has the usual piston (not shown), a connecting rod 23, and air passages carried in branch conduits 24 and 26 communicating to each end of the cylinder. A disk-shaped pressure foot member 27 is also provided at the lower end of connecting rod 24.

Air is provided under pressure from a suitable compressed air source at a pressure of higher than, say, about 100 pounds per square inch gage through supply line 28. This line is connected by means of conventional pipe fittings through valve 29 to main line 31 and branch line 32 to pressure gage 33. Main line 31 includes a filter 34 and pressure regulator 36. In order to support these components, line 31 is passed over a bracket 37, which is secured to horizontal member 18, and a U-strap 38 holds line 31 in place. Beyond the pressure regulator 36, there is a branch line 39 leading to pressure gage 41. Typically, the pressure will be reduced to about 60 pounds per square inch gage, and the reduced pressure will be indicated by gage 41.

At the end of main line 31, there is a switching valve 42 which switches the line pressure into either branch line 24 or 26 and thence to the air cylinder. Branch line 24 includes needle valve 43, and branch line 26 includes needle valve 44. In this way, the stroking pressure in the air cylinder may be adjusted for a desired stroking speed, with the up-and-down strokes being independently adjustable.

The switching valve 42 is operated by solenoid means in any of the usual solenoid valving arrangements. However, we prefer to use two separate solenoids, separately controlled for each switching movement. Thus solenoid 46 is used to move the valve into one position, and solenoid 47 is used to switch the valve into the other position. Thus in one position, main line 31 is connected to branch line 24, and branch line 26 is connected to an exhaust including muffler 50. With this valve position the cylinder extends to its full stroke. In the other position of switching valve 42, main line 31 is connected to branch line 22, and branch line 24 is connected to an exhaust including muffler 55. With this valve position the cylinder retracts to its full stroke.

Figure 7:
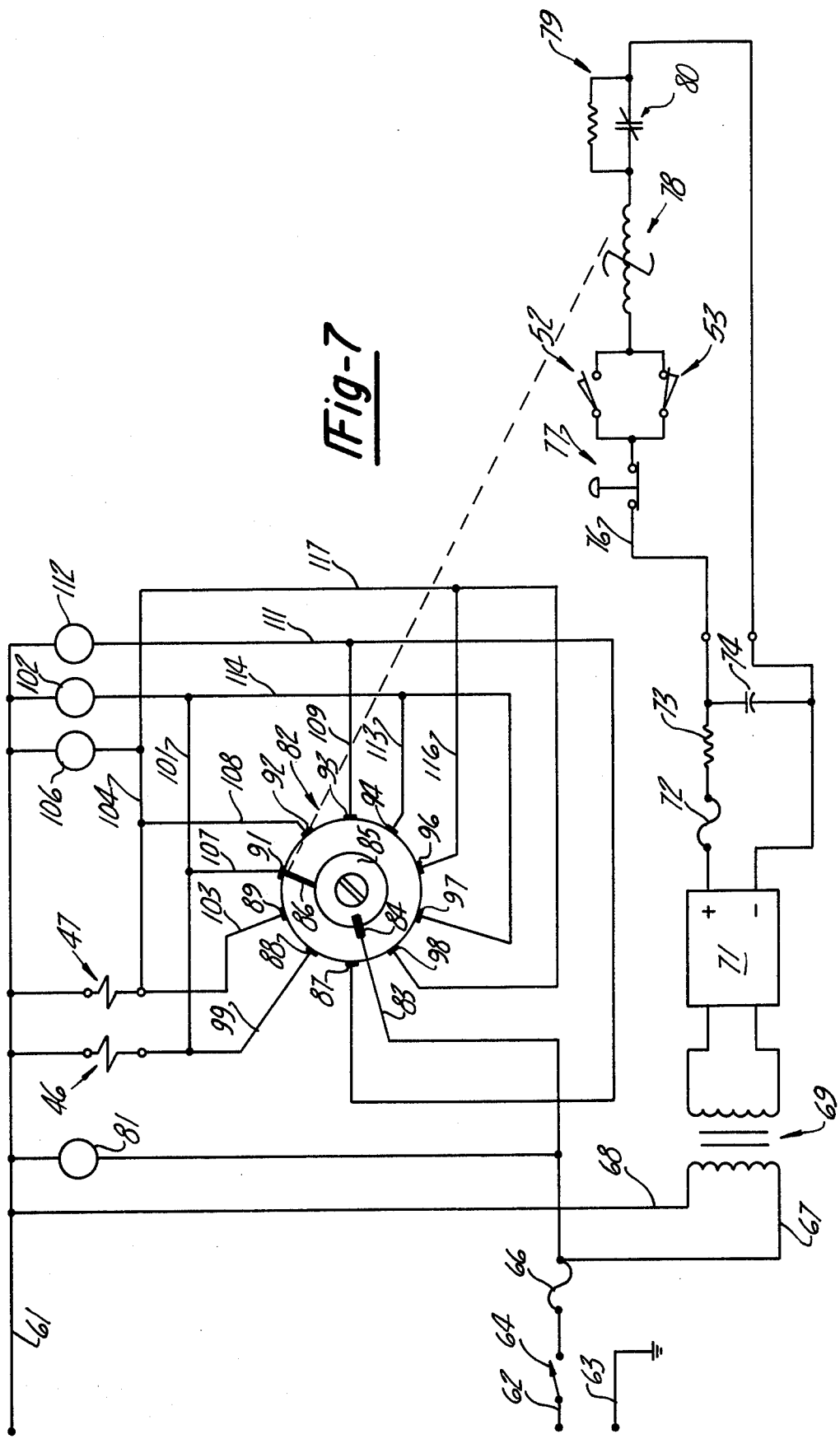
FIG. 7, a circuit diagram illustrating the operation of the electrical components.

In order to operate the solenoids, control circuitry is utilized as is illustrated in FIG. 7. Most of the control circuitry is contained in box 48 which is welded to frame member 17. Electrical connection is made between the two solenoids 46 and 47 and the box 48 through cables 49 and 51. As best seen in FIG. 3, limit switches 52 and 53 are provided to sense the retract and extend of the cylinder. These switches are also wired into the control box through appropriate wires (not shown).

Limit switch 52 is moved to a connected position on retract by movement of contact 54 on foot member 27 into contact and operating through a microswitch mechanism. This contact occurs each time the cylinder retracts. Foot member 27 is also provided with an upstanding rod 56 which carries contact 57 on its upper end, and thus contact 57 moves up and down along with foot member 27. As best seen in FIGS. 1 and 3, contact 57 operates limit switch 53 each time the cylinder extends.

Referring now to FIG. 7, there is shown a circuit diagram illustrating the electrical components and the wiring thereof. A three-plug 110 volt source is used from a standard outlet. The lines 61 and 62 carry the usual alternating current while the third wire 63 provides the usual safety ground. The line 62 carries main switch 64 and main fuse 66, and then two circuits are used. One of the circuits is used to operate the solenoids at full line voltage, and the other circuit operates the controls.

The control circuit includes lines 67 and 68 operating through the primary of transformer 69. The secondary is connected to a full wave rectifier bridge 71 to provide a 24 volt direct current fused at 72. The current is dampened to a more constant value through resistor 73 and condenser 74. Line 76 includes starting switch 77, limit switches 52 and 53 and a typical stepper including coil 78, interruptor contacts 80 mechanically operated by the coil for protecting same, and holding resistor 79 provided to maintain the circuit when the interruptor contacts are open. When the pulsing coil is operated, it provides a 36° movement of stepping switch 82 through a mechanical coupling for operation of the solenoids (see other circuit).

In operation, at the start, limit switch 52 is closed (retract position) and limit switch 53 is open. When switch 77 is opened and then closed, a pulse is provided and coil 78 will drive the stepping switch one step. As will be explained later, this will cause the cylinder to extend opening switch 53. On full extend switch 52 closes providing another pulse. Coil 78 then moves the stepping switch to the next position causing the cylinder to retract. This causes switch 52 to open, and on full retract swtich 53 closes to provide another pulse.

Referring now to the operating circuit, it is seen that when the switch 64 is closed, light 81 is turned on. In addition, connection is made to contact 83 of stepping switch 82, and thence to moving contact 86. Moving contact 86 goes through the circle of contacts 87, 88, 89, 91, 92, 92, 94, 96, 97 and 98 as it is pulsed by coil 78.

At the start, contact 86 is at 87 or 93. Assuming start at contact 87 only the cycle complete light 112 is provided with current through line 111. When the cycle start switch 77 is operated, the coil 78 moves contact 86 to contact 88. This energizes solenoid 46, which in turn moves switching valve 42 to supply compressed air to the cylinder on an extend stroke. At this time, a circuit is established through line 101 and extend light 102. At the end of the stroke, switch 53 causes a pulse to actuate coil 78 and move contact 86 to contact 89. This energizes solenoid 47, which in turn moves switching valve 42 to supply compressed air to the cylinder on a retract stroke. At this time, a circuit is established through line 104 and retract light 106. At the end of the stroke, switch 52 causes a pulse to actuate coil 78 and move contact 86 to contact 91. This energizes solenoid 46 and extend light 102 causes and an extend stroke as explained above. At the end of the stroke (which position is the one shown), switch 53 is energized causing a pulse to actuate coil 78 and move contact 86 to contact 92. This energizes solenoid 47 and retract light 106, with the solenoid moving the switching valve to cause a retract stroke. At the end of this stroke, switch 52 is energized causing a pulse to actuate coil 78 and move contact 86 to contact 93. In this position, cycle complete light 112 is turned on and the air cylinder stops.

In this way, the machine is operated to cause two down-and-up movements of the air cylinder and its associated pressure foot 27.

As here shown, the stepping switch 82 has 10 contacts, and only five are used for a cycle of operation. Thus two cycles are provided with the stepping switch shown. The second cycle of operation is similar to the first cycle. Thus operation of start switch 77 causes a pulse to move contact 86 to contact 94. Solenoid 46 and extend light 102 are energized to extend the cylinder as explained above. At the end of extend, switch 53 provides a pulse, contact 86 moves to contact 96, and solenoid 47 and retract light 106 are energized. This causes the cylinder to retract. At the end of this retract movement, switch 52 provides a pulse, contact 86 moves to contact 97, and solenoid 46 and extend light 102 are energized. Thus the cylinder extends. At the end of this extend movement, switch 53 provides a pulse, contact 86 moves to contact 98, and solenoid 47 and retract light 106 are energized. In this way, the cylinder retracts. At the end of this retract movement, switch 53 provides a pulse, and the coil 78 moves contact 86 to contact 87. This energizes the cycle complete light 112 and the cylinder movement stops at full retract.

Figure 4:
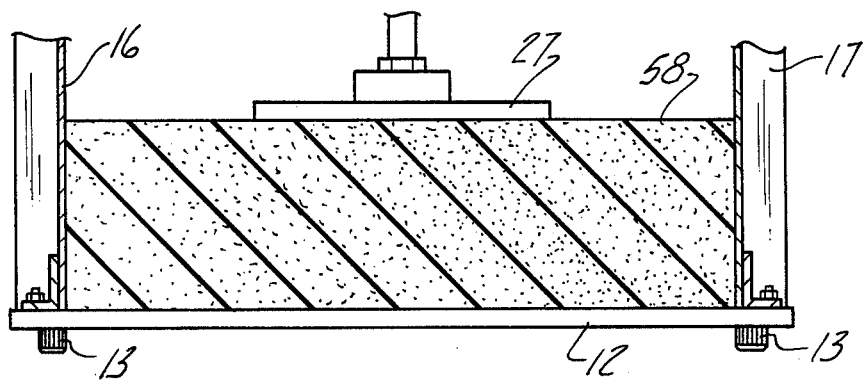
FIG. 4, a fragmentary sectional view of the machine of FIG. 1 as the flexing operation begins.
Figure 5:
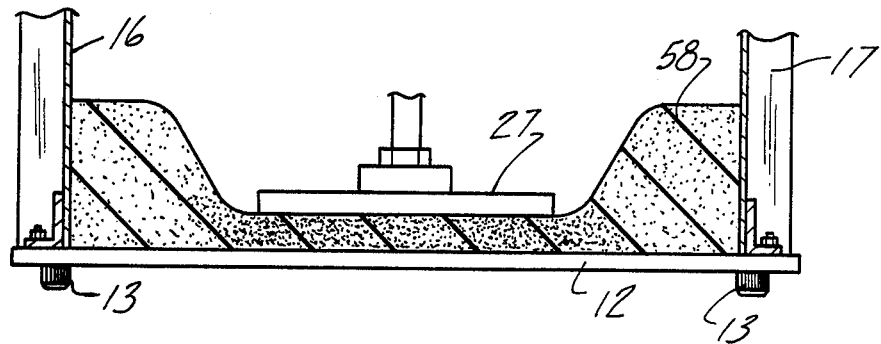
FIG. 5, a fragmentary sectional view of the machine of FIG. 1 at maximum flex.

In order to preflex a sample, a sample 58 of flexible foamed urethane is placed in position. The cycle start is actuated and the pressure foot begins its downward movement as the cylinder extends. As shown in FIG. 4, the cylinder has extended partly and is in contact with the sample. The extend continues until the position of FIG. 5 is reached. Then the retract stroke starts and during retract, the position of FIG. 4 is passed through again. The final retract position will be with the foot member spaced above the sample an amount sufficient to allow easy movement of the sample into and out of test position.

Figure 6:
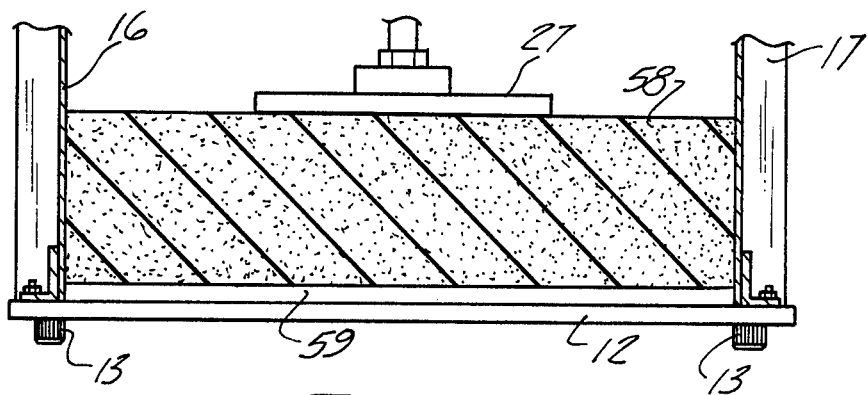
FIG. 6, a fragmentary sectional view of the machine of FIG. 1, as used to measure a sample of different thickness.

In the event that the sample is not as thick as the desired thickness, a shim 59 is provided as shown in FIG. 6. In addition, shims may be used to vary the extent of compression, if desired.

In the machine shown, the main design is used to compress a sample ¾ of its thickness twice. This corresponds with the test procedure now in use. In addition, the speed of movement of the air cylinders may be controlled by the air pressure regulator and needle valves. Thus test procedures may be varied as specifications are altered. In addition, the control components are separate, and more than two cycles can be provided simply by changing the circuit or possibly the stepping switch. However, once set up, the machine operates reliably through its program automatically and under the same conditions each time. In this way, operator error is eliminated and time is saved.

By using the preflexing machine in combination with a standard test machine in accordance with the invention, the standard test machine is used more efficiently. In addition, operator time heretofore required is eliminated, and tests may be run more rapidly.

The embodiments of the invention in which an exclusive property or privilege is claimed are defined as follows:

1. A flexing device for use in testing flexible foam articles comprising
   a bed for receiving samples in a testing position,
   support means carried on the bed,
   a fluid operated cylinder mounted on said support means,
   said cylinder comprising a piston, a first passage means for providing fluid to one side of the piston, a second passage means for providing fluid to the other side of the piston, and a pressure foot member attached to the piston and mounted to move into the testing position,
   conduit means for carrying fluid to and from said first and second passage means,
   a source of fluid under pressure in communication with said conduit means,
   an exhaust means,
   switching valve means for supplying fluid under pressure to one of said first and second passage means and for switching fluid from the other of said first and second passage means to said exhaust means,
   circuit means for operating the switching valve means comprising a stepping switch, solenoid means for operating the switching valve in positions corresponding to positions of the stepping switch, and a pulse operated drive mechanism for driving the stepping switch,
   first switch means mounted on said support means for actuation on an extended movement of the piston, and
   a second switch means mounted on said support means for actuation on a retracted movement of the piston
   said first and second switch means being located to provide pulses to said pulse operated drive mechanism whereby the stepping switch is moved at each end of the movement of the piston for providing automatic operation through the stepping switch sequence.

2. A flexing device as defined in claim 1, in which the fluid used is compressed air and the exhaust means comprises an exhaust line open to the outside, and muffler means on said exhaust line.

3. A flexing device as defined in claim 2, in which pressure reducing means is provided in said conduit means for controlling the pressure to the cylinder and speed of movement thereof.

4. A flexing device as defined in claim 1 the which shim means are provided to adjust the testing position of the bed with respect to the pressure foot member.

5. A flexing device for use in testing flexible foam articles comprising
   a bed for receiving samples in a testing position,
   support means carried on the bed,
   a fluid operated cylinder mounted on said support means,
   said cylinder comprising a piston, a first passage means for providing fluid to one side of the piston, a second passage means for providing fluid to the other side of the piston, and a pressure foot member attached to the piston and mounted to move into the testing position, supply conduit means for carrying fluid to and from said first and second passage means, a source of fluid under pressure in communication with said supply conduit means, a first and second exhaust conduit, switching valve means at the end of the supply conduit for supplying fluid under pressure to the first of said passage means while simultaneously connecting the second of said passage means to the second exhaust conduit in a first valve position and for supplying fluid under pressure to the second of said passage means while simultaneously connecting the first of said passage means to the first exhaust conduit in a second position, a first solenoid for moving the switching valve means to the first position, a second solenoid for moving the switching valve means to the second position, a first circuit means for operating the first and second solenoid comprising a stepping switch having at least one off position and a series of positions connecting alternately to the first and second solenoid, and a second circuit means comprising a pulse operated drive mechanism for driving the stepping switch sequentially thru its steps, and a plurality of switches for providing pulses to the drive mechanism, said plurality of switches comprising a start switch, and a first and second limit switch with the first limit switch carried on the support means in position for actuation at the end of an extend stroke of the piston and its associated moving parts and with the second limit switch carried on the support means in position for actuation at the end of a retract stroke of the piston and its associated moving parts.

6. A flexing device as defined in claim 5, in which the fluid used in compressed air and each exhaust conduit comprises a muffler and opens to the atmosphere.

7. A flexing device as defined in claim 6, in which a pressure reducing means is provided in the supply conduit means for controlling the pressure to the cylinder and thereby the speed of movement thereof.

8. A flexing device as defined in claim 5, in which shim means are provided to adjust the testing position of the bed with respect to the pressure foot member.

* * * * *

UNITED STATES PATENT AND TRADEMARK OFFICE
CERTIFICATE OF CORRECTION

PATENT NO. : 4,096,742
DATED : June 27, 1978
INVENTOR(S) : Thomas Carl Musolf and Harold Thomas Wyman It is certified that error appears in the above–identified patent and that said Letters Patent are hereby corrected as shown below:

Column 6, claim 4, line 54, after "claim 1, the word "the" should be ---in---.

Column 8, claim 6, line 16, after the word "used", the word "in" should be ---is---.

Signed and Sealed this

Nineteenth Day of December 1978

[SEAL]

Attest:

RUTH C. MASON
*Attesting Officer*

DONALD W. BANNER
*Commissioner of Patents and Trademarks*